United States Patent [19]

D'Silva

[11] Patent Number: 4,551,472
[45] Date of Patent: * Nov. 5, 1985

[54] UNSYMMETRICAL BIS-CARBAMATE COMPOUNDS

[75] Inventor: Themistocles D. J. D'Silva, Chapel Hill, N.C.

[73] Assignee: Union Carbide Corporation, Danbury, Conn.

[*] Notice: The portion of the term of this patent subsequent to Feb. 7, 1995 has been disclaimed.

[21] Appl. No.: 569,202

[22] Filed: Jan. 9, 1984

Related U.S. Application Data

[63] Continuation-in-part of Ser. No. 79,893, Sep. 28, 1979, abandoned, which is a continuation of Ser. No. 737,218, Nov. 14, 1976, abandoned, which is a continuation-in-part of Ser. No. 636,630, Dec. 1, 1975, abandoned.

[51] Int. Cl.$^4$ ............... A01N 47/12; A01N 47/22; C07C 161/00
[52] U.S. Cl. ............... 514/477; 260/453 RW; 260/453.3; 548/184; 260/465 D; 260/465.4; 549/14; 514/222; 514/229; 549/19; 514/369; 514/433; 549/21; 514/435; 514/436; 549/22; 514/438; 514/440; 549/28; 514/443; 514/447; 549/30; 514/452; 514/459; 549/32; 514/467; 514/469; 549/33; 514/472; 514/478; 549/38; 514/480; 544/58.2; 549/39; 544/145; 549/40; 549/59; 549/60; 549/68; 549/370; 549/371; 549/378; 549/414; 549/415; 549/419; 549/441; 549/448; 549/452; 549/467; 549/480; 560/134; 560/135; 560/136; 560/137; 560/148; 564/101

[58] Field of Search ........ 260/453 RW, 453.3, 465 D, 260/465.4; 424/270, 275, 276, 277, 278, 282, 283, 285, 298, 320; 544/58.2, 145; 548/184; 549/14, 19, 21, 22, 28, 30, 32, 33, 38, 39, 40, 59, 60, 68, 370, 371, 378, 414, 441, 415, 419, 448, 452, 467, 480; 560/134, 135, 136, 137, 148; 564/101; 514/222, 229, 369, 433, 435, 436, 438, 440, 443, 447, 452, 459, 467, 469, 472, 477, 478, 480

[56] References Cited

U.S. PATENT DOCUMENTS

| | | | |
|---|---|---|---|
| 3,679,733 | 7/1972 | Brown | 560/134 |
| 3,819,649 | 6/1974 | Zumach et al. | 549/38 |
| 3,890,386 | 7/1975 | Kuehle et al. | 564/102 |
| 3,950,374 | 4/1976 | Ueda et al. | 260/453 R |
| 3,954,836 | 5/1976 | Siegle et al. | 560/13 |
| 3,992,549 | 11/1976 | Durden et al. | 424/277 |
| 4,004,031 | 1/1977 | Drabek | 424/327 |
| 4,072,751 | 2/1978 | D'Silva | 424/298 |
| 4,081,550 | 3/1978 | D'Silva | 424/298 |
| 4,156,731 | 5/1979 | D'Silva | 424/277 |
| 4,327,110 | 4/1982 | D'Silva | 424/277 |

OTHER PUBLICATIONS

Kuehle et al., Chemical Abstracts, vol. 81, (1974), 169336x.
Kuehle et al., Chemical Abstracts, vol. 80, (1974), 145859y.
Siegle et al., Chemical Abstracts, vol. 84, (1976), 30719t.
Brown et al., Chemical Abstracts, vol. 77, (1972), 75032k.
Kuehle et al., Chemical Abstracts, vol. 78, (1973), 3756x.
Brown, Chemical Abstracts, vol. 81, (1974), 564j.

Primary Examiner—Richard L. Raymond
Attorney, Agent, or Firm—Gerald L. Coon

[57] ABSTRACT

Unsymmetrical N-substituted bis-carbamoyl sulfide compounds exhibit exceptional broad spectrum pesticidal activity coupled with extremely low mammalian toxicity and phytotoxicity.

31 Claims, No Drawings

UNSYMMETRICAL BIS-CARBAMATE COMPOUNDS

This application is a continuation-in-part of application Ser. No. 079,893 filed on Sept. 28, 1979, now abandoned, which in turn was a continuation of application Ser. No. 737,218 filed Nov. 14, 1976, now abandoned, which in turn was a continuation-in-part of application Ser. No. 636,630 filed on Dec. 1, 1975, now abandoned.

This invention relates to methods and compositions for controlling insect and acarid pests. In another aspect this invention relates to unsymmetrical N-substituted bis-carbamoyl sulfide compounds which are themselves novel and to their production.

The compounds which are employed as the active ingredients in the pesticidal compositions of this invention are unsymmetrical bis-carbamoyl sulfide compounds of the following general formula:

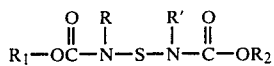

wherein:

R and R' are individually alkyl radicals having from 1 to 4 carbon atoms; $R_1$ is

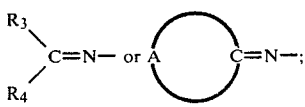

or $R_1$ is alkynyl when $R_2$ is other than alkenyl or alkynyl;

$R_2$ is other than $R_1$ and is alkenyl, alkynyl, phenyl, benzofuranyl, benzothienyl, naphthyl or tetrahydronaphthyl all of which may be either unsubstituted or substituted with one or more halogen, nitro, nitrile, alkyl, alkylthio, alkylthioalkyl, methylenedioxy, amino, alkylamino, dialkylamino, alkoxycarbonylamino, dialkylaminoalkylene-imino, alkylcarbonylamino, formylamino, dicyanoethylidene, alkoxy, alkynyloxy, phenoxy, phenyl, 2-dithianyl, 2-dithiolanyl, 2-dioxalanyl, 2-oxathianyl, 2-oxathialanyl or 2-dioxanyl groups in any combination; or $R_2$ is:

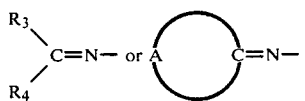

$R_3$ is hydrogen, alkyl, alkylthio or cyano; $R_4$ is alkyl, alkylthio, alkylthioalkyl, alkoxy alkanoyl aroyl or alkoxycarbonyl, all of which may be unsubstituted or aliphatically substituted in any combination with one or more cyano, nitro, alkylthio, alkylsulfinyl, alkylsulfonyl, alkoxy, aminocarbonyl, alkylaminocarbonyl, or dialkylaminocarbonyl groups or $R_4$ is phenyl, aminocarbonyl, alkylaminocarbonyl, dialkylaminocarbonyl or an $R_5CONH-$ or $R_5CON(alkyl)-$ group where $R_5$ is hydrogen, alkyl, or alkoxy; and A is a divalent aliphatic chain completing a five or six number ring, which includes one or two divalent oxygen, sulfur, sulfinyl or sulfonyl groups and which may also include one divalent amino, alkylamino or carbonyl group; in any combination; or A may also complete a six membered ring which includes three divalent sulfur, sulfinyl or sulfonyl groups in any combination; provided that the total number of aliphatic carbon atoms in $R_3$, $R_4$ and A individually, may not exceed eight.

The preferred compounds of this invention are those in which R and R' are methyl. The active compounds of this invention exhibit a very high level of pesticidal activity coupled with substantially reduced mammalian toxicity and plant phytotoxicity as compared with other known pesticidal compounds having a comparable spectrum of activity against insect, nematode and arachnid pests.

The unsymmetrical bis-carbamoyl sulfides of this invention can be prepared conveniently by the method shown in the following general reaction scheme:

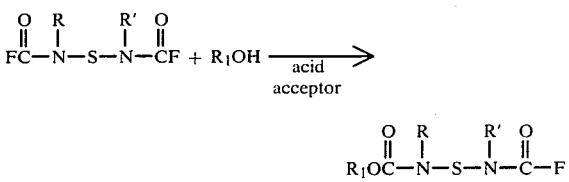

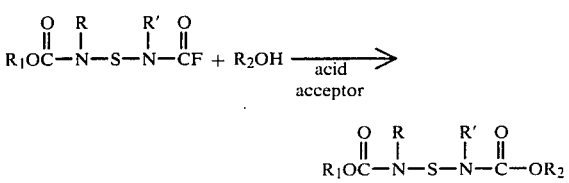

wherein R, R', $R_1$ and $R_2$ are as defined above.

One equivalent of an oxime or hydroxyl reactant ($R_1OH$ or $R_2OH$) is reacted with the bis-carbamoyl halide in the presence of one equivalent of an acid acceptor, preferably in an inert solvent to produce the intermediate carbamate-sulfenyl-carbamoyl halide compound which is then reacted with the second oxime or hydroxyl reactant. ($R_1OH$ if $R_2OH$ was used in the first step; $R_2OH$ if $R_1OH$ was used first) in the presence of an acid acceptor to yield the desired unsymmetrical bis-carbamate compound. The production of the intermediate carbamate-sulfenyl-carbamoyl halide compounds is described more fully in U.S. patent application Ser. No. 636,629 filed Dec. 1, 1975, entitled "Carbamate-Sulfenyl-Carbamoyl Compounds", now U.S. Pat. No. 4,338,450. The acid acceptor employed can be either an organic or inorganic base such as triethylamine or sodium or potassium hydroxide. A phase transfer agent such as a crown ether may also be employed. Any conventional inert solvent can be used, such as benzene, toluene, dioxane, tetrahydrofuran, ethyl ether, methylene chloride or the like.

This reaction may also be carried out in two phase systems such as an aqueous solution of an inorganic base as one phase and an aromatic solvent including a quaternary ammonium salt as a phase transfer agent as the second phase. The reaction temperature is not critical. The reaction goes essentially to completion at room temperature. Elevated temperatures may be employed if it is desired to reduce the reaction time.

The hydroxyl and oxime reactants employed in the synthesis described above are known compounds which can be prepared by conventional methods. See for example U.S. Pat. Nos. 3,752,841; 3,726,908; 3,843,669 and Belgian Pat. Nos. 813,206 and 815,513.

The bis-carbamoyl fluoride starting reactants are prepared by reacting hydrogen fluoride with an appropriately substituted alkylisocyante compound to form an alkylaminocarbonylfluoride compound which may then be reacted with sulfur dichloride to produce the desired bis-carbamoyl fluoride starting material.

Representative of an unsymmetrical bis-carbamoyl sulfide according to this invention is N-[2-Methylthio-2-methylpropionaldehyde-O-(N-methylcarbamoyl)oxime]N-[1-methylthioacetaldehyde O-(N-methylcarbamoyl)oxime]sulfide which has the structure:

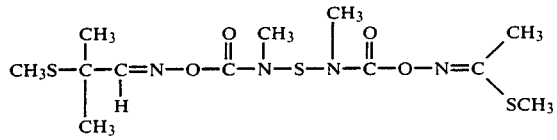

Other compounds illustrative of the new compounds of this invention are:

N-[1-Methylthioacetaldehyde O-(N-methylcarbamoyl)oxime]N-[2-O-(N-methylcarbamoyl)oximino-1,4-dithiane]sulfide
N-[1-Methylthioacetaldehyde O-(N-methylcarbamoyl)oxime]N-[2,3-dihydro-2,2-dimethyl-7-(N-methylcarbamoyloxy)benzofuran]sulfide
N-[1-Methylthioacetaldehyde O-(N-methylcarbamoyl)oxime]N-(3-isopropylphenyl N-methylcarbamate)sulfide
N-[1-Methylthioacetaldehyde O-(N-methylcarbamoyl)oxime]N-(1-naphthyl N-methylcarbamate)sulfide
N-[2-Methylthio-2-methylpropionaldehyde O-(N-methycarbamoyl)oxime]N-(1-naphthyl N-methylcarbamate)sulfide
N-[1-Methylthioacetaldehyde O-(N-methylcarbamoyl)oxime]N-(2-isopropoxyphenyl N-methylcarbamate)sulfide
N-[1-Methylthioacetaldehyde O-(N-methylcarbamoyl)oxime]N-(4-dimethylamino-3, 5-xylyl N-mehtylcarbamate)sulfide
N-[2-Methylthio-2-methylpropionaldehyde O-(N-methylcarbamoyl)oxime]N-(3-isopropyl-4-methoxycarbonylaminophenyl N-methylcarbamate)sulfide
N-[2-Methylthio-2-methylpropionaldehyde O-(N-methylcarbamoyl)oxime]N-[2,3-dihydro-2,2-dimethyl-7-(N-methylcarbamoyloxy)benzofuran]sulfide
N-[1-Methylthio-N',N'-dimethylcarbamoylformaldehyde O-(N-methylcarbamoyl)oxime]N-[1-methylthioacetaldehyde O-(N-methylcarbamoyl)oxime]sulfide
N-[2-Methylsulfonyl-2-methylpropionaldehyde O-(N-methylcarbamoyl)oxime]N-[2,3 dihydro-2,2-dimethyl-7-(N-methylcarbamoyloxy)benzofuran]sulfide
N-[2-O-(N-methylcarbamoyl)oximino-1,4-dithiane]N-(3-isopropylphenyl N-methylcarbamate)sulfide
N-[1-Methylthioacetaldehyde O-(N-methylcarbamoyl)oxime]N-[4-(N',N'-dmethylformamidino)-B 3,5-xylyl N-methylcarbamate]sulfide
N-[1-Methylthioacetaldehyde O-(N-methylcarbamoyl)oxime]N-[(N',N'-dimethylaminomethylenecarbamoyl)-1-methylthioformaldehyde O-(N-methylcarbamoyl)oxime]sulfide
N-[2-Methylthio-2-methylpropionaldehyde O-(N-methylcarbamoyl)oxime]N-(4-dimethylamino-3,5-xylyl N-methylcarbamate)sulfide
N-[3,3-Dimethyl-1-methylthiobutanone-2 O-(N-methylcarbamoyl)oxime]N-[1-methylthioacetaldehyde O-(N-methylcarbamoyl)oxime]sulfide
N-[3,3-Dimethyl-1-methylsulfonylbutanone-2 O-(N-methylcarbamoyl)oxime]N-[2,3-dihydro-2,2-dimethyl-7-(N-methylcarbamoyloxy)benzofuran]sulfide
N-[3-Methylsulfonylbutanone-2 O-(N-methylcarbamoyl)oxime]N-[2,3-dihydro-2,2-dimethyl-7-(N-methylcarbamoyloxy)benzofuran]sulfide
N-[3,3-Dimethyl-1-methylthiobutanone-2 O-(N-methylcarbamoyl)oxime]N-[1-methylthioacetaldehyde O-(N-methylcarbamoyl)oxime]sulfide
N-[2-Cyano-2-methylpropionaldehyde O-(N-methylcarbamoyl)oxime]N-(1-naphthyl N-methylcarbamate)sulfide
N-[1-Methylthio-N',N'-dimethylcarbamoylformaldehyde O-(N-methylcarbamoyl)oxime]N-[2,3-dihydro 2,2-dimethyl-7-(N-methylcarbamoyloxy)benzofuran]sulfide
N-[1-Methylthiopyruvaldehyde O-(N-methylcarbamoyl)oxime]N-[1-methylthioacetaldehyde O-(N-methylcarbamoyl)oxime]sulfide
N-[2-O-(N-methylcarbamoyl)oximino-1,3-dithiolane]N-(1-naphthyl N-methylcarbamate)sulfide
N-[5-Methyl-4 O-(N-methylcarbamoyl)oximino-1,3-dithiolane]N-(1-naphthyl N-methylcarbamate)sulfide
N-[1-(2-cyanoethylthio)acetaldehyde O-(N-methylcarbamoyl)oxime]N-(1-naphthyl N-methylcarbamate)sulfide
N-[1-(2-cyanoethylthio)acetaldehyde O-(N-methylcarbamoyl)oxime]N-[2,3-dihydro-2,2-dimethyl-7-(N-methylcarbamoyloxy)benzofuran]sulfide
N-[4,5,5-Trimethyl-2 O-(N-methylcarbamoyl)oximinothiazolidin-3-one]N-[1-methylthioacetaldehyde O-(N-methylcarbamoyl)oxime]sulfide
N-[4,5,5-Trimethyl-2O-(N-methylcarbamoyl)oximinothiazolidin-3-one]N-[3,5,5-trimethyl-2 O-(N-methylcarbamoyl)oximinothiazolidin-4-one]sulfide
N-[4-Methyl-2, O-(N-methylcarbamoyl)oximino-tetrahydro-1,4-thiazine-3-one]N-(1-naphthyl N-methylcarbamate)sulfide
N-[4-Methyl-2 O-(N-methylcarbamoyl)oximino-tetrahydro-1,4-thiazine-3-one]N-[1-(2-cyanoethylthio)acetaldehyde O-(N-methylcarbamoyl)oxime]sulfide
N-[4-Methyl-2 O-(N-methylcarbamoyl)oximino-tetrahydro-1,4-thiazine-3-one]N-[1-methyltioacetaldehyde O-(N-methylcarbamoyl)oxime]sulfide
N-[5,5-Dimethyl-4 O-(N-methylcarbamoyl)oximino 1,3-dithiolane]N-(1-naphthyl N-methylcarbamate)sulfide
N-[2-(O-(N-methylcarbamoyl)oximino-1,4-dithiane]N-[4-dimethylamino-3,5-xylyl N-methylcarbamate]sulfide
N-[2-(O-(N-methylcarbamoyl)oximino-1,4-dithiane]N-[3-isopropyl-4-methoxycarbonylamino-(N-methylcarbamoyloxy)benzene)sulfide
N-[1-(2-cyanoethylthio)acetaldehyde O-(N-methylcarbamoyl)oxime]N-[2-(2-dithiolanyl)phenyl N-methyl carbamate]sulfide.
N-[1-(2-cyanoethylthio)acetaldehyde O-(N-methylcarbamoyl)oxime]N-[2-(2-dioxalanyl)phenyl-N-methylcarbamate]sulfide.
N-[1-isopropylthioacetaldehyde O-(N-methylcarbamoyl)oxime]N-[2-propynyloxy phenyl N-methylcarbamate]sulfide
N-[2,3-dihydro-2,2-dimethyl-7-benzofuranyl-N-methylcarbamate]N-[propynyl N-methyl carbamate]sulfide.
N-[1-(2-cyanoethylthio)acetaldehyde O-(N-methylcarbamoyl)oxime]N-[4-phenoxyphenyl N-methylcarbamate]sulfide.

N-[1-Methylthio-N',N'-dimethylcarbamoylformaldehyde O-(N-methylcarbamoyl)oxime]N-[2-(2-dithiolanyl)phenyl N-methylcarbamate]sulfide N-[1-(2-cyanoethylthioacetaldehyde O-(N-methylcarbamoyl)oxime]N-[2-isopropoxyphenyl N-methylcarbamate]sulfide N-[2-O-(N-methylcarbamoyl)oximino-1,3,5-trithiane]N-[2-isopropoxyphenyl N-methylcarbamate]sulfide N-[2-O-(N-methylcarbamoyl)oximino-1,3,5-trithiane]N-[2-(2-oxathiolanyl)phenyl N-methylcarbamate]sulfide.

N-[2-O-(N-methylcarbamoyl)oximino-1,4-dithiane]N-[2-propynyloxy phenyl N-methylcarbamate]sulfide N-[5-Methyl-4-O-(N-methylcarbamoyl)oximino-oxathiolane]N-[4-phenoxyphenyl N-methylcarbamate]sulfide.

N-[4,5,5-Trimethyl-2-O-[N-methylcarbamoyl)oximino-thiazolidin-3-one]N-[2-propynyloxy phenyl N-methylcarbamate]sulfide N-[3,5,5-Trimethyl-2-O-[N-methylcarbamoyl]oximino-thiazolidin-4-one]N-[2-(2-dithiolanyl)phenyl N-methylcarbamate]sulfide.

The following specific examples are provided to illustrate the procedures used for the preparation of the compounds of this invention.

EXAMPLE I

Preparation of N-[2-Methylthio-2-methylpropionaldehyde O-(N-methylcarbamoyl)oxime]N-[1-methylthioacetaldehyde O-(N-methylcarbamoyl)oxime]sulfide A. To a polypropylene reactor containing 80 g (4.0 m) of hydrogen fluoride in 1800 ml of toluene, cooled to $-40°$ C. was added dripwise with stirring 228 g (4.0 m) of methylisocyanate, over a period of 20 minutes. The reaction mixture was allowed to warm to 0° C. and was maintained at this temperature for 1 hour. Then 206 g (2 m) of freshly distilled sulfur dichloride was added followed by a slow addition of 346 g (4.4 m) of pyridine at $-20°$ to 0° C. After stirring for 2 hours at $-10°$ C. and for 16 hours at ambient temperatures, the reaction mixture was diluted with 500 ml of water. The toluene layer was further washed with (3×500 ml) water dried and distilled to yield 244 g (66 percent) of bis-(N-methyl-N-fluorocarbonylamino)sulfide.

B.p. 55°–57° C./0.25 mm. m.p. 40°–41° C.

Calc'd for $C_4H_6F_2N_2O_2S$: C, 26.09; H, 3.28; N, 15.21 Found: C, 26.19; H, 3.20; N, 14.79.

B. To a solution of 0.714 g of 1-methylthioacetaldoxime and 1.36 g of bis-(N-methyl-N-fluorocarbonylamino sulfide in 15 ml dioxane was added dropiwse 0.687 g of triethylamine. After the solution was allowed to stand for 20 hours, it was diluted with water and extracted with ethyl acetate. The organic extract was washed with water, dried with magnesium sulfate and concentrated under vacuum to yield 1.0 g of 1-methylthioacetaldehyde O-[N-methyl-N-(N'-methyl-N'-fluoroformylaminosulfenyl)carbamoyl]oxime which was crystallized from isopropyl ether-ethyl acetate, m.p. 102°–104° C.

Calc'd for $C_7H_{12}FN_3O_3S_2$: C, 31.22; H, 4.49; N, 15.60 Found: C, 31.67; H, 4.69; N, 15.34

C. To a solution of 2.69 g of 1-methylthioacetaldehyde O-[N-methyl-N-(N'-fluoroformylaminosulfenyl)-carbamoyl]oxime and 1.33 g 2-methylthio-2-methylpropionalkoxime in 50 m dioxane was a with stirring 1.01 g triethylamine. After 48 hours the reaction mixture was diluted with water and extracted in ethylacetate. The organic extract was washed with water, dried and concentrated. The product, N-[2-Methylthio-2-metylpropionaldehyde O-(N-methylcarbamoyl)oxime]N-[1-methylthioacetaldehyde O-(N-methylcarbamoyl)oxime]sulfide, was crystallized from isopropyl ether. Wt. of solid 1.87 g. m.p. 99°–101° C.

Calc'd for $C_{12}H_{22}N_4O_4S_3$: C, 37.68; H, 5.80; N, 14.65; Found: C, 37.68; H, 5.72; N, 14.51.

EXAMPLE II

Preparation of N-[1-Methylthioacetaldehyde O-(N-methylcarbamoyl)oxime]N-[2-(O-N-methylcarbamoyl)oximino)-1,4-dithiane]sulfide To a solution of 2.69 g of 1-methylthioacetaldehyde O-[N-methyl N-(N'-methyl-N'-fluoroformylaminosulfenyl)carbamoyl]oxime and 2-oximino-1,4-dithiane in 50 ml of dioxane was added dropwise with stirring 1.01 g of triethylamine. After stirring at ambient temperature for 48 hours the solid was collected by filtration. It was then dissolved in methylene chloride, washed with water, dried and concentrated to yield 2.2 g of N-[1-Methylthioacetaldehyde O-(N-methylcarbamoyl)oxime]N-[2-O-(N-methylcarbamoyl)oximino-1,4-dithiane]sulfide. Crystallized from ethyl acetate chloroform. m.p. 164°–165° C.

Calc'd for $C_{11}H_{18}N_4O_4S_4$: C, 33.15; H, 4.55; N, 14.06; Found: C, 33.06; H, 4.55; N, 13.80.

EXAMPLE III

Preparation of N-[2-(O-(N-methylcarbamoyl)oximino]-1,4-dithiane]-N-[2-O-(N-methylcarbamoyl)oximino-3,5,5-trimethyl-thiazolidin-4-one]sulfide To a suspension of 3.4 g of 2-[O-(N-methyl-N-(N'-methyl-N'-fluoroformylaminosulfenyl)carbamoyl)oximino]-3,5,5-trimethylthiazolidin-4-one and 1.5 g of 2-oximio-1,4-dithiane in 70 ml of toluene cooled to 15° C., was added dropwise with stirring 1.05 g of triethylamine over a period of 20 minutes. After stirring for 17 hours at room temperature the reaction mixture was concentrated under reduced pressure. The solid was taken in methylene chloride, washed with water. The organic layer was dried and concentrated to yield 3.5 g of N-[2-(N-methylcarbamoyl)oximino-1,4-dithiane]N-[2-O-(N-methylcarbamoyl)oximino-3,5,5-triethyl-thiazolidin-4-one]sulfide. Recrystallized from ethyl acetate and isopropyl ether. m.p. 170°–171° C.

Calc'd for $C_{14}H_{21}N_5O_5S_4$: C, 35.96; H, 4.53; N, 14.98; Found: C, 35.90; H, 4.94; N, 14.75.

EXAMPLE IV

Preparation of N-[N-methyl-N-propargyloxycarbonylamino]N-[3,5,5-trimethylthiazolidin-4-one-2 O-(N-methylcarbamoyl)oxime]sulfide To a solution of 1.7 g of 2-[O-(N-methyl-N-(N'-methyl-N'-fluoroformylaminosulfenyl)carbamoyl)oximino]-3,5,5-trimethylthiazolidin-4-one and 0.28 g of propargyl alcohol in 20 ml of toluene cooled to 10°–15° C. was added dropwise 0.55 g of triethylamine dissolved in 5 ml of toluene. After stirring for 20 hours at ambient temperature, the reaction mixture was diluted with water and ethyl acetate. The organic extract was washed with water, dried over anhydrous magnesium sulfate and concentrated under reduced pressure. The product, N-[N-methyl-N-propargyloxycarbonylamino]N-[3,5,5-trimethylthiazolidin-4-one-2-O-(N-methylcarbamoyl)oxime]sulfide, was crystallized from isopropyl ether-ethylacetate.

Weight=0.52 g m.p. 96°-96.8° C.

Calc'd for $C_{13}H_{18}N_4O_5S_2$: C, 41.70; H, 4.84; N, 14.96; Found: C, 41.86; H, 5.06; N, 14.22.

EXAMPLE V

Preparation of N-[1-Methylthioacetaldehyde O-(N-methylcarbamoyl)oxime]N-[2,2-dimethyl-2,3-dihydro-7-(N-methylcarbamoyloxy)benzofuran]sulfide To a solution of 5.0 g of 1-methylthioacetaldehyde O-[N-methyl-N-(N'-methyl-N'-fluoroformylaminosulfenyl)carbamoyl]oxime and 3.05 g of 2,2-dimethyl-2,3-dihydrobenzofuran-7-ol in 50 ml of dioxane was added dropwise 1.87 g of triethylamine. After allowing the reaction mixture to stand for 18 hours, it was quenched with 200 ml of water and the product was extracted with ethyl acetate. The organic extract was washed with water, dried over magnesium sulfate and concentrated under reduced pressure to yield an oil. The product, N-[1-methylthioacetaldehyde O-(N-methylcarbamoyl)oxime]N-[2,2-dimethyl-2,3-dihydro-7-(N-methylcarbamoyloxy)benzofuran]sulfide, crystallized from ethylacetate-isopropyl ether. Weight of solid 4.3 g m.p. 141°-144° C.

Calc'd for $C_{17}H_{23}N_3O_5S_2$: C, 49.38; H, 5.60; N, 10.16; Found: C, 49.59; H, 5.63; N, 10.34.

EXAMPLE VI

Preparation of N-[2-Methylthio-2-methylpropionaldehyde O-(N-methylcarbamoyl)oxime]N-[1-(N-methylcarbamoyloxy)naphthalene]sulfide To a solution of 6.5 g of 1-[N-methyl-N-(N'-methyl-N'-fluoroformylaminosulfenyl)carbamoyloxy]naphthalene and 2.94 g of 2-methylthio-2-methylpropionaldoxime in 100 ml of toluene was added 2.23 g of triethylamine and the reaction mixture stirred for 18 hours. The mixture was diluted with an additional 100 ml of toluene and was washed with a 100 percent solution of sodium carbonate and water. The organic phase was dried and concentrated under vacuo to yield 7.7 g of the crude N-[2-Methylthio-2-methylpropionaldehyde O-(N-methylcarbamoyl)oxime]N-[1-methylcarbamoyloxynaphthalene]sulfide as a viscous oil. An aliquot was purified by dry column chromatography.

Calc'd for $C_{19}H_{23}N_3O_4S_2$: C, 54.13; H, 5.50; N, 9.96; Found: C, 53.19; H, 5.56; N, 9.58.

EXAMPLE VII

Preparation of N-[1-Methylthioacetaldehyde O-(N-methylcarbamoyl)oxime][N-1-1-naphthyl N-methylcarbamate]sulfide N-[1-Methylthioacetaldehyde O-(N-methylcarbamoyl)oxime]N-[1-naphthylmethylcarbamate]sulfide was prepared by the procedure employed in Example VI by reacting 3.88 g of 1-methylthioacetaldehyde O-[N-methyl-N-(N'-methyl N'-fluoroformylaminosulfenyl)carbamoyl]oxime with 2.07 g of 1-naphthol and 1.45 g of triethylamine as an acid acceptor.

Weight of product 4.1 g. m.p. 88°-90° C.

Calc'd for $C_{17}H_{19}N_3O_4S_2$: C, 51.89; H, 4.87; N, 10.68; Found: C, 52.35; H, 4.86; N, 10.31.

EXAMPLE VIII

Preparation of N-[1-Methylthioacetaldehyde O-(N-methylcarbamoyl)oxime]N-[4-isopropylphenyl-(N-methylcarbamoyl sulfide N-[1-Methylthioacetaldehyde O-(N-methylcarbamoyl)oxime]N-[4-isopropylphenyl-(N-methylcarbamoyloxy)]sulfide was prepared by the procedure employed in Example VI by reacting 3.56 g of 1-methylthioacetaldehyde O-[N-methyl-N-(N'-methyl-N'-fluoroformylaminosulfenyl)carbamoyl]oxime with 2.04 g of 4-isopropylphenol and 1.51 g of triethylamine as an acid acceptor.

Weight of the product 3.7 g m.p. 108°-110° C.

Calc'd for $C_{16}H_{23}N_3O_4S_2$: C, 49.85; H, 6.01; N, 10.90; Found: C, 49.22; H, 6.07; N, 10.97.

EXAMPLE IX

Preparation of N-[1-Methylthioacetaldehyde O-(N-methylcarbamoyl)oxime]N-[4-tert-butylphenyl-(N-methylcarbamoyloxy)]sulfide N-[1-Methylthioacetaldehyde (O-(N-methylcarbamoyl)oxime]N-[4-tert-butylphenyl-(N-methylcarbamoyloxy)]sulfide was prepared by the procedure employed in Example VI by reacting 3.56 g of 1-methylthioacetaldehyde O-[N-methyl-N-(N'-methyl-N'-fluoroformylaminosulfenyl)carbamoyl]oxime with 2.25 g of 4-tert-butylphenol and 1.51 g of triethylamine as an acid acceptor. Weight of the product was 3.8 g, m.p. 141°-143° C.

Weight for $C_{17}H_{25}N_3O_4S_2$: C, 51.10; H, 6.30; N, 10.51; Found: C, 50.69; H, 6.37; N, 10.59.

EXAMPLE X

Preparation of N-[1-Methylthioacetaldehyde O-(N-methylcarbamoyl oxime]N-[1-(2-cyanoethylthio)acetaldehyde O-(N-methylcarbamoyl oxime]sulfide N-[1-Methylthioacetaldehyde O-(N-methylcarbamoyl)oxime]N-[1-(2-cyanoethylthio)acetaldehyde O-(N-methylcarbamoyl oxime]sulfide was prepared by the procedure employed in Example III by reacting 2.88 g of 1-(2-cyanoethyl)thioacetaldoxime and 4.75 g of 1-methylthioacetaldehyde O-[N-methyl-N-(N'-methyl-N'-fluoroformylaminosulfenyl)carbamoyl]oxime in 75 ml of toluene and 2.02 g of triethylamine as an acid acceptor. Weight of the product 5.2 g m.p. 121°-123° C.

Calc'd for $C_{12}H_{19}N_5O_4S_3$: C, 36.62; H, 4.87; N, 17.80; Found: C, 36.48; H, 4.81; N, 17.44.

EXAMPLE XI

Preparation of N-[1-Methylthioacetaldehyde O-(N-methylcarbamoyl)oxime]N-[1-methylthio-N', N'-dimethylcarbamoylformaldehyde O-(N-methylcarbamoyl)oxime]sulfide N-[1-Methylthioacetaldehyde O-(N-methylcarbamoyl)oxime]N-[1-methylthio-N', N'-dimethylcarbamoylformaldehyde O-(N-methylcarbamoyl)oxime]sulfide was prepared by the procedure employed in Example III by reacting 5.39 g of 1-methylthioacetaldehyde O-[N-methyl-N-(N'-methyl-N'-fluoroformylaminosulfenyl)carbamoyl]oxime with 3.24 g of 1-methylthio-N,N-dimethylcarbamoylformaldoxime in 100 ml of toluene and 2.02 g of triethylamine as an acid acceptor. Weight of recrystallized product 4.0 g m.p. 121°-123° C.

Calc'd for $C_{12}H_{21}N_5O_5S_3$: C, 35.02; H, 5.14; N, 17.02; Found: C, 35.00; H, 5.18; N, 16.58.

EXAMPLE XII

Preparation of N-[1-Methylthioacetaldehyde O-(N-methylcarbamoyl)oxime]N-[1-(N-methylcarbamoyloxy)-4-nitrobenzene]sulfide N-[1-Methylthioacetaldehyde O-(N-methylcarbamoyl)oxime]N-[1-(N-methylcarbamoyloxy)-4-nitrobenzene]sulfide was prepared by the procedure employed in Example V by reacting 5.0 g of 1-methylthioacetaldehyde O-[N-methyl-N-(N'-methyl N'-fluoroformylaminosulfenyl)carbamoyl]oxime with 2.59 g of 4-nitrophenol in 75 ml of dioxane and 1.87 g of triethylamine. Weight of the product 3.9 g. m.p. 164°–165° C.

Calc'd for $C_{13}H_{16}N_4O_6S_2$: C, 40.20; H, 4.15; N, 14.42; Found: C, 40.35; H, 4.05; N, 14.23.

EXAMPLE XIII

Preparation of N-[1-Methylthioacetaldehyde O-(N-methylcarbamoyl)oxime]N-[1-methylthio-1-ethoxycarbonylformaldehyde O-(N-methylcarbamoyl)oxime]sulfide N-[1-Methylthioacetaldehyde O-(N-methylcarbamoyl)oxime]N-[1-methylthio-1-ethoxycarbonylformaldehyde O-(N-methylcarbamoyl)oxime]sulfide was prepared by the procedure employed in Example III by reacting 5.38 g of 1-methylthioacetaldehyde O-[N-methyl-N-(N'-methyl-N'-fluoroformylaminosulfenyl)-carbamoyloxime] with 3.26 g of 1-methylthio-1-ethoxycarbonylformaldoxime in 75 ml of toluene and 2.02 g of triethylamine as an acid acceptor. Weight of the product 6.02 g. m.p. 99°–100° C.

Calc'd for $C_{12}H_{20}N_4O_6S_3$: C, 34.94; H, 4.89; N, 13.58; Found: C, 34.76; H, 5.00; N, 13.41.

EXAMPLE XIV

Preparation of N-[1-Methylthioacetaldehyde O-(N-methylcarbamoyl)oxime]N-[1-(N-methylcarbamoyloxy)-5,6,7,8-tetrahydronaphthalene]sulfide N-[1-Methylthioacetaldehyde O-(N-methylcarbamoyl)oxime]N-[1-(N-methylcarbamoyloxy)-5,6,7,8-tetrahydronaphthalene]sulfide was prepared by the procedure employed in Example VI by reacting 2.0 g of 1-methylthioacetaldehyde O-[N-methyl-N-(N'-methyl-N'-fluoroformylaminosulfenyl)carbamoyl]oxime with 1.1 g of 5,6,7,8-tetrahydro-1-naphthol in 50 ml of toluene and 0.75 g of triethylamine as an acid acceptor. Weight of the product 2.3 g. m.p. 119°–120° C.

Calc'd for $C_{17}H_{23}N_3O_4S_2$: C, 51,36; H, 5.83; N, 10.57; Found: C, 51.16; H, 5.86; N, 10.44.

EXAMPLE XV

Preparation of N-[1-Methylthioacetaldehyde O-(N-methylcarbamoyl)oxime]N-[O-(N-methylcarbamoyl)-4-methylthio-3-methylphenyl]sulfide N-[1-Methylthioacetaldehyde O-(N-methylcarbamoyl)oxime]N-[O-(N-methylcarbamoyl)-4-methylthio-3-methylphenyl]sulfide was prepared by the procedure employed in Example VI by reacting 3.56 g of 1-methylthioacetaldehyde O-(N-methyl-N-(N'-methyl-N'-fluoroformylaminosulfenyl)carbamoyl]oxime with 2.77 g of 4-(methylthio)-m-cresol in 100 ml of toluene and 1.81 g of triethylamine as an acid acceptor. Weight of the product 3.2 g. m.p. 98°–99° C.

Calc'd for $C_{15}H_{21}N_3O_4S_3$: C, 44.64; H, 5.24; N, 10.41; Found: C, 44.40; H, 5.08; N, 10.25.

EXAMPLE XVI

Preparation of N-[1-Methylthioacetaldehyde O-(N-methylcarbamoyl)oxime]N-[4methoxycarbonylamino-(N-methylcarbamate)-3-isopropylphenyl]sulfide N-[1-Methylthioacetaldehyde O-(N-methylcarbamoyl)oxime]N-[4-methoxycarbonylamino-(N-methylcarbamate)-3-isopropylphenyl]sulfide was prepared by the procedure employed in Example VI by reacting 4.0 g of 1-methylthioacetaldehyde O-[N-methyl-N-(N'-methyl-N'-fluoroformylaminosulfenyl)carbamoyl]oxime with 3.75 g of 4-methoxycarbonylamino-3-isopropylphenol in 75 ml of toluene and 1.81 g of triethylamine as an acid acceptor. Weight of the product 3.6 g. m.p. 113°–115° C.

Calc'd for $C_{18}H_{26}N_4O_6S_2$: C, 47.14; H, 5.72; N, 12.22; Found: C, 46.86; H, 6.05; N, 12.11.

EXAMPLE XVII

Preparation of N-[1-Methylthioacetaldehyde O-(N-methylcarbamoyl)oxime]N-[3-(and 4)-isopropylphenyl-(N-methylcarbamoyloxy)]sulfide N-[1-Methylthioacetaldehyde O-(N-methylcarbamoyl)oxime]N-[3-(and 4)-isopropylphenyl-(N-methylcarbamoyloxy)]sulfide was prepared by the procedure employed in example VI by reacting 2.69 g of 1-methylthioacetaldehyde O-[N-methyl-N-(N'-methyl-N'-fluoroformylaminosulfenyl)carbamoyl]oxime with 1.36 g of meta/para-(60:40)-isopropylphenol in 50 ml of dioxane and 1.01 g of triethylamine as an acid acceptor. Weight of the crude product 2.18 g. An aliquot was purified by chromatography.

Calc'd for $C_{16}H_{23}N_3O_4S_2$: C, 49.85; H, 6.01; N, 10.90; Found: C, 48.14; H, 5.90; N, 11.07.

EXAMPLE XVIII

Preparation of N-[1-Methylthioacetaldehyde O-(N-methylcarbamoyl)oxime]N-[3,4,5-trimethylphenyl-(N-methylcarbamoyloxy)]sulfide N-[1-Methylthioacetaldehyde O-(N-methylcarbamoyl)oxime]N-[3,4,5-trimethylphenyl-(N-methylcarbamoyloxy)]sulfide was prepared by the procedure employed in Example VI by reacting 3.55 g of 1-methylthioacetaldehyde O-[N-methyl-N-(N'-methyl-N'-fluoroformylaminosulfenyl)carbamoyl]oxime with 2.72 g of 3,4,5-trimethylphenol in 100 ml of toluene using 2.02 g of triethylamine as an acid acceptor. Weight of the product 3.1 g. m.p. 97°–99° C.

Calc'd for $C_{16}H_{23}N_3O_4S_2$: C, 49.85; H, 6.01; N, 10.90; Found: C, 49.57; H, 5.97; N, 10.89.

EXAMPLE XIX

Preparation of N-[-Methylthioacetaldehyde O-(N-methylcarbamoyl)oxime]N-[2,4-dinitro-6-sec-butylphenyl-(N-methylcarbamoyloxy)]sulfide N-[1-Methylthioacetaldehyde O-(N-methylcarbamoyl)oxime]N-[2,4-dinitro-6-sec-butylphenyl-(N-methylcarbamoyloxy)]sulfide was prepared by the procedure employed in Example VI by reacting 3.56 g of 1-methylthioacetaldehyde O-[N-methyl-N-(N'-methyl-N'-fluoroformylaminosulfenyl)carbamoyl]oxime with 4.3 g of 2,4-dinitro-6-sec-butylphenol in 100 ml of toluene and 1.8 g of triethylamine as an acid acceptor. Crystallized from methanol. m.p. 129°–130° C.

Calc'd for $C_{17}H_{23}N_5O_8S_2$: C, 41.71; H, 4.74; N, 14.31; Found: C, 41.60; H, 4.52; N, 14.22.

EXAMPLE XX

Preparation of N-[1-Methylthioacetaldehyde O-(N-methylcarbamoyl)oxime]N-[3-(N',N'-dimethylamino)phenyl-(N-methyl carbamoyloxy)]sulfide N-[1-Methylthioacetaldehyde O-(N-methylcarbamoyl)oxime]N-[3-(N',N'-dimethylamino)phenyl-(N-methylcarbamoyloxy)]sulfide was prepared by the procedure employed in Example VI by reacting 3.55 g of 1-methylthioacetaldehyde O-[N-methyl-N-(N'-methyl-N'-fluoroformylaminosulfenyl)carbamoyl]oxime with 1.78 g of 3-dimethylaminophenol in 150 ml of toluene and 1.52 g of triethylamine as an acid acceptor. The weight of the product after purification 1.3 g m.p. 108°–109° C.

Calc'd for $C_{15}H_{22}N_4O_4S_2$: C, 46.61; H, 5.74; N, 14.50; Found: C, 46.33; H, 5.52; N, 14.19.

EXAMPLE XXI

Preparation of N-[1-Methylthioacetaldehyde O-(N-methylcarbamoyl)oxime]N-[4-formylamino-3-methylphenyl-(N-methylcarbamoyloxy)]sulfide N-[1-Methylthioacetaldehyde O-(N-methylcarbamoyl)oxime]N-[4-formylamino-3-methylphenyl-(N-methylcarbamoyloxy)]sulfide was prepared by the procedure employed in Example VI by reacting 4.04 g of 1-methylthioacetaldehyde O-[N-methyl-N-(N'-methyl-N'-fluoroformylaminosulfenyl)carbamoyl]oxime with 2.67 g of 4-N,N-dimethylformamidino-metacresol in 200 ml of toluene and 1.56 g of triethylamine as an acid acceptor. After usual work-up and purification by column chromatography 0.7 g of the product was isolated. m.p. 143°–145° C.

Calc'd for $C_{15}H_{20}N_4O_5S_2$: C, 44.98; H, 5.03; N, 13.99; Found: C, 44.87; H, 4.98; N, 13.79.

EXAMPLE XXII

Preparation of N-[2-(O-(N-methylcarbamoyl)oximino)-1,4-dithiane]N-[1-naphthyl-(N-methylcarbamoyloxy)]sulfide N-[2-O-(N-methylcarbamoyl)oximino-1,4-dithiane]N-[1-naphthyl-(N-methylcarbamoyloxy)]sulfide was prepared by the procedure employed in Example VI by reacting 5.0 g of 1-[N-methyl-N-(N'-methyl-N'-fluoroformylaminosulfenyl)carbamoyloxy]-naphthalene with 2.42 g of 2-oximino-1,4-dithiane in 100 ml of toluene and 1.64 g of triethylamine as an acid acceptor. Weight of the product 5.0 g. m.p. 148°–150° C.

Calc'd for $C_{18}H_{19}N_3O_4S_3$: C, 49.41; H, 4.38; N, 9.60; Found: C, 48.70; H, 4.28; N, 9.53.

EXAMPLE XXIII

Preparation of N-[1-Methylthioacetaldehyde O-(N-methylcarbamoyl)oxime]N-[4-cis,7)-octadienyl-(N-methylcarbamoyloxy)benzene]sulfide N-[1-Methylthioacetaldehyde O-(N-methylcarbamoyl)oxime]N-[4-(2-cis,7)octadienyl-(N-methylcarbamoyloxy)benzene]sulfide was prepared by the procedure employed in Example VI by reacting 3.5 g of 1-methylthioacetaldehyde O-[N-methyl-N-(N'-methyl-N'-fluoroformylaminosulfenyl)carbamoyl]oxime with 2.63 g of 4-(cis 2,7)-octadienylphenol in 150 ml of toluene and 1.31 g of triethylamine as an acid acceptor. The oily residue was purified by column chromatography to yield 1.9 g of an oil.

Calc'd for $C_{21}H_{29}N_3O_4S_2$: C, 55.85; H, 6.47; N, 9.30; Found: C, 55.22; H, 6.39; N, 9.22.

EXAMPLE XXIV

Preparation of N-[2-O-(N-methylcarbamoyl)oximino-1,4-dithiane]N-[2,3-dihydro-2,2-dimethyl-7-(N-methylcarbamoyloxy)-benzofuran]sulfide N-[2-(O-(N-methylcarbamoyl)oximino)-1,4-dithiane]N-[2,3-dihydro-2,2-dimethyl-7-(N-methylcarbamoyloxy)benzofuran]sulfide was prepared by the procedure employed in Example VI by reacting 3.13 g of 2-[O-[N-methyl-N-(N'-methyl-N'-fluoroformylaminosulfenyl)carbamoyl]oximino]-1,4-dithiane with 1.65 g of 2,3-dihydro-2,2-dimethyl-benzofuran-7-ol in 150 ml of toluene and 1.01 g of triethylamine as an acid acceptor. The crude product was purified by dry-column chromatography to yield an amorphous solid.

Calc'd for $C_{18}H_{23}N_3O_5S_3$: C, 47.24; H, 5.07; N, 9.18; Found: C, 46.04; H, 5.03; N, 8.81.

EXAMPLE XXV

Preparation of N-[2-O-(N-methylcarbamoyl)oximino-1,4-dithiane]N-[4-isopropyl-(N-methylcarbamoyloxy)benzene]sulfide N-[2-(O-(N-methylcarbamoyl)oximino)-1,4-dithiane]N-[4-isopropyl-(N-methylcarbamoyloxy)benzene]sulfide was prepared by the procedure employed in Example VI by reacting 3.13 g of 2-O-[N-methyl-N-(N'-methyl-N'-fluoroformylaminosulfenyl)carbamoyl]oximino-1,4-dithiane with 1.36 g of 4-isopropylphenol in 150 ml of toluene and 1.01 g of triethylamine. Weight of the product after column chromatography 1.1 g. m.p. 129°–131° C.

Calc'd for $C_{17}H_{25}N_3O_4S_3$: C, 47.53; H, 5.40; N, 9.70; Found: C, 47.40; H, 5.27; N, 9.73.

The compounds of EXAMPLES XXVI–XLI were prepared by the methods of EXAMPLES I–XXV. The physical properties of these compounds are listed in TABLE I below.

TABLE I

MELTING POINTS AND ELEMENTAL ANALYSIS OF CARBAMOYLOXIME COMPOUNDS $$R_1-O\overset{\underset{\Vert}{O}}{C}-\overset{\underset{|}{R}}{N}-S-\overset{\underset{|}{R'}}{N}-\overset{\underset{\Vert}{O}}{C}O-R_2$$

| Example | $R_1$ | $R_2$ | R | R' | MP °C. | Molecular Formula | Calculated/Found C | H | N |
|---|---|---|---|---|---|---|---|---|---|
| XXVI | 1-naphthyl | —CH$_2$C≡CH | —CH$_3$ | —CH$_3$ | Oil | C$_{17}$H$_{16}$N$_2$O$_4$S | 59.29/ 59.45 | 4.68/ 4.57 | 8.14/ 8.00 |
| XXVII | 2,4-dimethylphenyl | —CH$_2$C≡CH | —CH$_3$ | —CH$_3$ | Oil | C$_{15}$H$_{18}$N$_2$O$_4$S | 55.88/ 55.18 | 5.63/ 5.42 | 8.69/ 8.82 |
| XXVIII | H$_3$C—C(SCH$_3$)=N— | 3-isopropylphenyl | —CH$_3$ | —CH$_3$ | 63–65 | C$_{16}$H$_{23}$N$_3$O$_4$S$_2$ | 49.74/ 49.85 | 6.08/ 6.01 | 10.84/ 10.90 |
| XXIX | H$_3$C—C(SCH$_3$)=N— | 2-chloro-4-tert-butylphenyl | —CH$_3$ | —CH$_3$ | 139–140 | C$_{17}$H$_{24}$ClN$_3$O$_4$S$_2$ | 47.04/ 46.92 | 5.57/ 5.48 | 9.68/ 9.79 |
| XXX | H$_3$C—C(SCH$_3$)=N— | 4-dodecylphenyl | —CH$_3$ | —CH$_3$ | 74–77 | C$_{25}$H$_{41}$N$_3$O$_4$S$_2$ | 58.67/ 58.01 | 8.02/ 8.06 | 8.21/ 8.44 |
| XXXI | H$_3$C—C(SCH$_3$)=N— | 4-nonylphenyl | —CH$_3$ | —CH$_3$ | 65–68 | C$_{22}$H$_{35}$N$_3$O$_4$S$_2$ | 56.26/ 56.40 | 7.51/ 7.69 | 8.95/ 8.93 |
| XXXII | H$_3$C—C(SCH$_3$)=N— | 4-biphenyl | —CH$_3$ | —CH$_3$ | 126–127 | C$_{19}$H$_{21}$N$_3$O$_4$S$_2$ | 54.39/ 53.76 | 5.05/ 4.73 | 10.02/ 10.06 |
| XXXIII | H$_3$C—C(SCH$_3$)=N— | 2-methoxy-4-allylphenyl | —CH$_3$ | —CH$_3$ | 96–98 | C$_{17}$H$_{23}$N$_3$O$_5$S$_2$ | 49.37/ 49.08 | 5.60/ 5.56 | 10.16/ 10.19 |
| XXXIV | H$_3$C—C(SCH$_3$)=N— | 4-phenoxyphenyl | —CH$_3$ | —CH$_3$ | 129–130 | C$_{19}$H$_{21}$N$_3$O$_5$S$_2$ | 52.40/ 52.26 | 4.86/ 4.65 | 9.64/ 9.69 |
| XXXV | H$_3$C—C(SCH$_3$)=N— | 3-phenoxyphenyl | —CH$_3$ | —CH$_3$ | 98–100 | C$_{19}$H$_{21}$N$_3$O$_5$S$_2$ | 52.40/ 52.05 | 4.86/ 4.72 | 9.64/ 9.56 |
| XXXVI | H$_3$C—C(SCH$_3$)=N— | 2-(1,3-dithiolan-2-yl)phenyl | —CH$_3$ | —CH$_3$ | 81–83 | C$_{16}$H$_{21}$N$_3$O$_4$S$_4$ | 42.92/ 42.75 | 4.73/ 4.61 | 9.39/ 9.34 |
| XXXVII | H$_3$C—C(SCH$_3$)=N— | 2-(1,3-dioxolan-2-yl)phenyl | —CH$_3$ | —CH$_3$ | Oil | C$_{16}$H$_{21}$N$_3$O$_6$S$_2$ | 46.26/ 46.02 | 5.10/ 5.13 | 10.11/ 9.92 |

TABLE I-continued
MELTING POINTS AND ELEMENTAL ANALYSIS OF CARBAMOYLOXIME COMPOUNDS $$R_1-OC(O)-N(R)-S-N(R')-CO-R_2$$

| Example | R₁ | R₂ | R | R' | MP °C. | Molecular Formula | Calculated/Found C | H | N |
|---|---|---|---|---|---|---|---|---|---|
| XXXVIII | H₃C—C(SCH₃)=N— | —O—C₆H₄—CH(CH₃)₂ | —CH₃ | —CH₃ | 96–97 | C₁₆H₂₃N₃O₅S₂ | 47.86/47.36 | 5.77/5.57 | 10.47/10.39 |
| XXXIX | H₃C—C(SCH₃)=N— | —C₆H₄—OCH₂C≡CH | —CH₃ | —CH₃ | 110–111 | C₁₆H₁₉N₃O₅S₂ | 48.35/48.49 | 4.28/4.84 | 10.57/10.33 |
| XL | H₃C—C(SCH₃)=N— | —N=C(S-CH₂-CH₂-S) (thiazoline) | —CH₃ | —CH₃ | 182–185 | C₁₀H₁₆N₄O₄S₅ | 28.83/28.47 | 3.87/3.83 | 13.45/13.01 |
| XLI | H₃C—C(SCH₃)=N— | —N=C(CH₃)—C(O)—C₆H₅ | —CH₃ | —CH₃ | 155–157 | C₁₆H₂₀N₄O₅S₂ | 46.58/46.62 | 4.88/4.93 | 13.58/13.49 |

Selected species of the new compounds were evaluated to determine their pesticidal activity against mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°–70° F. and 50–70 percent relative humidity, consisted with test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Bait Test

Larvae of the southern armyworm (*Spodopera eridania*, (Cram.)), reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80±5° F. and 50±5 percent relative humidity, were the test insects.

The test compounds were formulated by diluting the stock suspension with water to give a suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss strapy gun set at 10 psig air pressure. This application, which lasted 25 seconds, was sufficient to wet plants to run-off. As a control, 100-110 milliliters of a water-acetone-emulsifier solution containing no test compound were also strayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (Musca domestica, L.), reared according to the specifications of the Chemical Specialties Manufacturing Association (Blue Book, McNair-Dorland Co., N.Y. 1954; pages 243-244, 261) under controlled conditions of 80±5° F. and 50±5 percent relative humidity, were the test insects. The flies were immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty-four hours, at a temperature of 80±5° F. and the relative humidity of 50±5 percent. Flies which showed no sign of movement on prodding were considered dead.

Mite Foliage Spray Test

Adults and nymphal stage of the two-spotted mite (*Tetranychus urticae* Koch), reared on Tendergreen bean plants at a temperature of 80±5° F. and at a relative humidity of 50±5 percent, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty-four hours. Following the twenty-four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun at 40 psig. air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at a temperature of 80±5° F. and a 50±5 percent relative humidity for six days, after which a mortality count of motile forms was made. Microscopic examination for motile forms was made on the leaves of the test plants. Any individual which was capable of locomotion upon prodding was considered living.

Nematocide Test

The test organism used was the infective migratory larvae of the root-knot nematode, *Meloidogyne incognita* var. acrita, reared in the greenhouse on roots of cucumber plants. Infected plants were removed from the culture, and the roots are chopped very finely. A small amount of this inoculum was added to a pint jar containing approximately 180 cc. of soil. The jars were capped and incubated for one week at room temperature. During this period eggs of the nematode were hatched, and the larval forms migrated into the soil.

Ten ml. of the test formulation were added to each of the two jars for each dosage tested. Following the addition of chemical, the jars were capped, and the contents thoroughly mixed on a ball mill for 5 minutes.

The test compounds were formulated by a standard procedure of solution in acetone addition of an emulsifier, and dilution with water. Primary screening tests were conducted at 3.33 m.g. of the test compound per jar.

The jars were left capped at room temperature for a period of 48 hours, and the contents then transferred to 3 inch pots. Subsequently, the pots were seeded to cucumber as an indicator crop and placed in the greenhouse where they were cared for in the normal fashion for approximately 3 weeks.

The cucumber plants were then taken from the pots, the soil removed from the roots; and the amount of galling visually rated.

The results of these tests are set forth in Table I below. In these tests the pesticidal activity of the compounds at the indicated dosage rate against aphid, mite, Southern Armyworm (SA), Mexican Bean Beetle (MBB), and house fly was rated as follows:
 A=excellent control
 B=partial control
 C=no control
 In the test for activity against nematodes (nem) activity was rated as follows:
 1=severe galling, equal to untreated plants
 2=moderate galling
 3=light galling
 4=very light galling
 5=no galling, perfect control
Dashes indicate no test conducted.

Phytotoxicity Test

Experiments were also conducted to determine the phytotoxicity of representative compounds with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the foliage to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

Mammalian Toxicity

Certain compounds were also evaluated to determine their peroral toxicity to mammals by conventional methods. The representative animal selected for this experiment was the rat. The test results obtained are expressed in terms of the number of milligrams of composition per kilogram of weight of the animal required to achieve a mortality rate of 50 percent ($LD_{50}$).

The results of these experiments are also summarized in Table I below.

TABLE II

Biological Activity

| Example | Compound | Aphid | Mite | S.A. | M.B.B. | Fly | Nem | A.O. Rat Mg/Kg | Phytotoxicity Bean | Corn | Tom | Cotton | Soy |
|---------|----------|-------|------|------|--------|-----|-----|----------------|--------------------|------|-----|--------|-----|
| I | CH$_3$—C(OCH$_3$)=NOCN(CH$_3$)—S—N(SCH$_3$)—C(=O)—O—N=C(CH$_3$)—C(H)(CH$_3$)—SCH$_3$ | A | A | A | A | A | 5 | 2.1 | 2 | 1 | 1 | 2 | 1 |
| II | CH$_3$—C(OCH$_3$)=NOC(=O)—N(CH$_3$)—S—N(SCH$_3$)—C(=O)—O—N= (dithiane) | A | A | A | A | A | 5 | 190.0 | 1 | 1 | 1 | 1 | 1 |
| III | CH$_3$(NOC)—N(OCH$_3$)—S—N(CH$_3$)—C(=O)—O—N= (dithiane); thiazolidinone ring | C | A | A | A | A | 1 | 160 | 1 | 2 | 1 | 2 | 2 |
| IV | CH$_3$(NOCN)—N(OCH$_3$)—S—N(CH$_3$)—C(=O)—O—CH$_2$—C≡CH; thiazolidinone ring | B | C | A | A | A | 1 | — | 1 | 1 | 2 | 2 | 2 |
| V | CH$_3$—C(OCH$_3$)=NOCN(CH$_3$)—S—N(SCH$_3$)—C(=O)—O—(2,2-dimethyl-2,3-dihydrobenzofuran-7-yl) | A | C | A | A | A | 5 | 15.9 | 2 | 1 | 2 | 2 | 2 |

TABLE II-continued

| Example | Compound | Biological Activity | | | | | | A.O. Rat Mg/Kg | Phytotoxicity | | | | |
|---|---|---|---|---|---|---|---|---|---|---|---|---|---|
| | | Aphid | Mite | S.A. | M.B.B. | Fly | Nem | | Bean | Corn | Tom | Cotton | Soy |
| VI | CH₃S—C(CH₃)(CH₃)—C(OCH₃)=NOCN(CH₃)—S—N(H)—C(O)—O-(1-naphthyl) | A | A | A | A | A | 4 | 2.97 | 1 | 1 | 1 | 1 | 1 |
| VII | CH₃—C(SCH₃)=NOC(O)—N(CH₃)—S—N(CH₃)—C(O)—O-(1-naphthyl) | A | B | A | A | A | 4 | 160.0 | 1 | 1 | 1 | 2 | 2 |
| VIII | CH₃—C(SCH₃)=NOC(O)—N(CH₃)—S—N(CH₃)—C(O)—O—C₆H₄—CH(CH₃)₂ | A | C | A | A | A | 4 | 160.0 | 1 | 1 | 1 | 1 | 1 |
| IX | CH₃—C(SCH₃)=NOC(O)—N(CH₃)—S—N(CH₃)—C(O)—O—C₆H₄—C(CH₃)₃ | A | C | A | A | A | 3 | 226.0 | 1 | 1 | 1 | 1 | 1 |
| X | CH₃—C(SCH₃)=NOC(O)—N(CH₃)—S—N(CH₃)—C(O)—O—N=C(CH₃)—NCCH₂CH₂S | A | A | A | A | A | 1 | 67.3 | 1 | 1 | 1 | 2 | 1 |

TABLE II-continued

Biological Activity

| Example | Compound | Aphid | Mite | S.A. | M.B.B. | Fly | Nem | A.O. Rat Mg/Kg | Bean | Corn | Tom | Cotton | Soy |
|---|---|---|---|---|---|---|---|---|---|---|---|---|---|
| XI | CH₃−C(OCH₃)=NOCN(CH₃)−S−N(SCH₃)−C(=O)−O−N=C(CN)−SCH₂CH₃ | A | A | A | A | A | — | 14.1 | 1 | 1 | 1 | 2 | 1 |
| XII | CH₃−C(OCH₃)=NOCN(CH₃)−S−N(SCH₃)−C(=O)−O−C₆H₄−NO₂ | A | C | A | A | A | 1 | 453.0 | 1 | 1 | 1 | 1 | 1 |
| XIII | CH₃−C(OCH₃)=NOCN(CH₃)−S−N(SCH₃)−C(=O)−O−N=C(COC₂H₅)−SCH₃ | A | A | A | A | A | 3 | 160.0 | 1 | 1 | 1 | 1 | 2 |
| XIV | CH₃−C(OCH₃)=NOCN(CH₃)−S−N(SCH₃)−C(=O)−O−(5,6,7,8-tetrahydronaphthyl) | A | C | A | A | A | 4 | 285.0 | 1 | 1 | 1 | 1 | 1 |
| XV | CH₃−C(OCH₃)=NOC(=O)N(CH₃)−S−N(CH₃)−C(=O)−O−C₆H₃(CH₃)(SCH₃) | A | C | A | A | A | 4 | 40.0 | 1 | 1 | 1 | 1 | 1 |

TABLE II-continued

| | | Biological Activity | | | | | | A.O. Rat Mg/Kg | Phytotoxicity | | | | |
|---|---|---|---|---|---|---|---|---|---|---|---|---|---|
| Example | Compound | Aphid | Mite | S.A. | M.B.B. | Fly | Nem | | Bean | Corn | Tom | Cotton | Soy |
| XVI | ![structure] CH₃-C(=NOC(=O)N(CH₃)-S-N(CH₃)-C(=O)OCH₃)-SCH₃ attached to phenyl with CH(CH₃)₂ and HN-C(=O)OCH₃ substituents | B | C | A | A | A | 4 | 28.3 | 1 | 1 | 1 | 1 | 1 |
| XVII | ![structure] CH₃-C(=NOC(=O)N(CH₃)-S-N(OCH₃)(CH₃))-SCH₃ attached to phenyl-CH(CH₃)₂ (mix. m,p isomers) | A | B | A | A | A | 4 | 126.0 | 1 | 1 | 1 | 1 | 1 |
| XVIII | ![structure] CH₃-C(=NOC(=O)N(CH₃)-S-N(OCH₃)(CH₃))-SCH₃ attached to 3,4,5-trimethylphenyl | A | C | A | A | A | 4 | 95.1 | 1 | 1 | 1 | 1 | 1 |
| XIX | ![structure] CH₃-C(=NOC(=O)N(CH₃)-S-N(OCH₃)(CH₃))-SCH₃ attached to phenyl with CH(CH₃)(CH₂CH₃), O₂N, and NO₂ substituents | A | A | A | A | A | 1 | — | 1 | 2 | 2 | 2 | 2 |

TABLE II-continued

| Example | Compound | Biological Activity | | | | | | A.O. Rat Mg/Kg | Phytotoxicity | | | | |
|---|---|---|---|---|---|---|---|---|---|---|---|---|---|
| | | Aphid | Mite | S.A. | M.B.B. | Fly | Nem | | Bean | Corn | Tom | Cotton | Soy |
| XX | CH₃—C(=NOC(O)N(CH₃)—S—N(CH₃)(CH₃))—SCH₃ ; 3-(N,N-dimethylamino)phenyl ester | A | B | A | A | A | 4 | — | 1 | 1 | 1 | 2 | 2 |
| XXI | CH₃—C(=NOC(O)N(OCH₃)(CH₃)—S—N(CH₃))—SCH₃ ; 4-(2-methyl-formamidophenyl) ester | A | A | A | A | A | 4 | — | 1 | 1 | 1 | 1 | 1 |
| XXII | NOC(O)N(OCH₃)(CH₃)—S—N= (1,3-dithian-2-ylidene); 1-naphthyl ester | B | C | A | A | A | 4 | 453.0 | 1 | 1 | 1 | 1 | 2 |
| XXIII | CH₃—C(=NOC(O)N(OCH₃)(CH₃)—S—N(CH₃))—SCH₃ ; 4-(CH₂=CHCH₂CH₂CH₂CH=CHCH₂)phenyl ester | A | C | A | A | A | — | — | — | — | — | — | — |

TABLE II-continued

Biological Activity

| Example | Compound | Aphid | Mite | S.A. | M.B.B. | Fly | Nem | A.O. Rat Mg/Kg | Phytotoxicity Bean | Corn | Tom | Cotton | Soy |
|---|---|---|---|---|---|---|---|---|---|---|---|---|---|
| XXIV | (2,2-dimethyl-2,3-dihydrobenzofuran-7-yl carbamate with OCH₃, CH₃, NOCN-S- dithiane) | A | A | A | A | A | 5 | 20. | 1 | 1 | 1 | 2 | 2 |
| XXV | (4-isopropylphenyl carbamate with OCH₃, CH₃, NOC-N-S- dithiane) | A | A | A | A | A | — | — | 1 | 1 | 1 | 3 | 1 |
| XXVI | (1-naphthyl propargyl carbamate with OCH₃, CH₃, CN-S-N-C-OCH₂C≡CH) | A | C | A | A | A | 4 | — | 1 | 1 | 1 | 1 | 2 |
| XXVII | (3,4-dimethylphenyl propargyl carbamate with OCH₃, CH₃, CN-S-N-C-OCH₂C≡CH) | A | B | A | A | A | 5 | — | 1 | 1 | 1 | 2 | 2 |

TABLE II-continued

| Example | Compound | Aphid | Mite | S.A. | M.B.B. | Fly | Nem | A.O. Rat Mg/Kg | Bean | Corn | Tom | Cotton | Soy |
|---------|----------|-------|------|------|--------|-----|-----|----------------|------|------|-----|--------|-----|
| | | | | | | | | | | | Phytotoxicity | | |
| XXVIII | CH₃—C=NOCN—S—N—C—O—⟨phenyl⟩—CH(CH₃)₂ (OCH₃, CH₃, SCH₃) | A | C | A | A | A | — | 40 | 1 | 1 | 1 | 2 | 2 |
| XXIX | CH₃—C=NOCN—S—N—C—O—⟨phenyl-Cl⟩—C(CH₃)₃ (OCH₃, CH₃, SCH₃) | A | B | A | A | A | 5 | — | 1 | 1 | 1 | 1 | 1 |
| XXX | CH₃—C=NOCN—S—N—C—O—⟨phenyl⟩—C₁₂H₂₅ (OCH₃, CH₃, SCH₃) | A | B | A | A | A | 4 | — | 1 | 1 | 1 | 2 | 1 |
| XXXI | CH₃—C=NOCN—S—N—C—O—⟨phenyl⟩—C₉H₁₉ (OCH₃, CH₃, SCH₃) | A | C | A | A | A | 5 | >640 | 1 | 1 | 1 | 1 | 1 |

TABLE II-continued

| Example | Compound | Biological Activity | | | | | | A.O. Rat Mg/Kg | Phytotoxicity | | | | |
|---------|----------|-------|------|------|------|-----|-----|--------|------|------|-----|--------|-----|
| | | Aphid | Mite | S.A. | M.B.B. | Fly | Nem | | Bean | Corn | Tom | Cotton | Soy |
| XXXII | $\begin{array}{c} \text{OCH}_3 \quad \text{CH}_3 \quad \text{O} \\ \text{CH}_3-\text{C}=\text{NOCN}-\text{S}-\text{N}-\text{C}-\text{O}-\text{C}_6\text{H}_4-\text{C}_6\text{H}_5 \\ \mid \\ \text{SCH}_3 \end{array}$ | A | C | A | A | A | 4 | — | 2 | 1 | 1 | 2 | 1 |
| XXXIII | $\begin{array}{c} \text{OCH}_3 \quad \text{CH}_3 \quad \text{O} \\ \text{CH}_3-\text{C}=\text{NOCN}-\text{S}-\text{N}-\text{C}-\text{O-Ar} \\ \mid \\ \text{SCH}_3 \end{array}$ (2-OCH$_3$, 4-CH$_2$CH=CH$_2$ phenyl) | A | B | A | A | A | 5 | — | 1 | 1 | 1 | 3 | 1 |
| XXXIV | $\begin{array}{c} \text{O} \quad \text{CH}_3 \quad \text{CH}_3 \quad \text{O} \\ \text{CH}_3-\text{C}=\text{NOC}-\text{N}-\text{S}-\text{N}-\text{C}-\text{O}-\text{C}_6\text{H}_4-\text{OC}_6\text{H}_5 \\ \mid \\ \text{SCH}_3 \end{array}$ | A | B | A | A | A | — | >640 | 1 | 1 | 1 | 1 | 1 |
| XXXV | $\begin{array}{c} \text{OCH}_3 \quad \text{CH}_3 \quad \text{O} \\ \text{CH}_3-\text{C}=\text{NOCN}-\text{S}-\text{N}-\text{C}-\text{O}-\text{C}_6\text{H}_4-\text{OC}_6\text{H}_5 \\ \mid \\ \text{SCH}_3 \end{array}$ | A | C | A | A | A | — | — | 1 | 1 | 1 | 1 | |
| XXXVI | $\begin{array}{c} \text{OCH}_3 \quad \text{CH}_3 \quad \text{O} \\ \text{CH}_3-\text{C}=\text{NOCN}-\text{S}-\text{N}-\text{C}-\text{O-Ar} \\ \mid \\ \text{SCH}_3 \end{array}$ (2-CH(SCH$_2$CH$_2$CH$_2$S) phenyl) | A | C | A | A | A | 4 | 50.4 | 1 | 1 | 1 | 1 | 1 |

TABLE II-continued

| | | Biological Activity | | | | | | A.O. Rat Mg/Kg | Phytotoxicity | | | | |
|---|---|---|---|---|---|---|---|---|---|---|---|---|---|
| Example | Compound | Aphid | Mite | S.A. | M.B.B. | Fly | Nem | | Bean | Corn | Tom | Cotton | Soy |
| XXXVII | CH₃—C(OCH₃)=NOCN(CH₃)—S—N(SCH₃)—C(O)—O—[2-(1,3-dioxolan-2-yl)phenyl] | A | A | A | A | A | 4 | — | 2 | 1 | 1 | 2 | 2 |
| XXXVIII | CH₃—C(OCH₃)=NOCN(CH₃)—S—N(SCH₃)—C(O)—O—[2-(CH(CH₃)OCH₃)phenyl] | A | A | A | A | A | — | 63.5 | 1 | 1 | 1 | 1 | 2 |
| XXXIX | CH₃C(OCH₃)=NOCN(CH₃)—S—N(SCH₃)—C(O)—O—[2-(OCH₂C≡CH)phenyl] | A | A | A | A | A | 3 | 160 | 1 | 1 | 1 | 2 | 2 |
| XL | CH₃—C(OCH₃)=NOCN(CH₃)—S—N(SCH₃)—C(O)—O—N=C(1,3-dithiolan-2-ylidene) | B | C | A | A | A | 5 | — | 1 | 1 | 1 | 1 | 1 |
| XLI | CH₃—C(OCH₃)=NOCN(CH₃)—S—N(SCH₃)—C(O)—O—N=C(CH₃)—C(O)—C₆H₅ | A | B | A | A | A | 1 | — | 1 | 1 | 1 | 1 | 1 |

Several of the unsymmetrical bis-carbamoyl sulfide compounds of this invention were tested against related known compounds. The results, in terms of $LD_{50}$ values are summarized in Table III. The term "i" denotes inactivity at 500 ppm which indicates that the $LD_{50}$ value is significantly in excess of 500 ppm. The data in Table III shows that the tested compounds of this invention have a broader spectrum of excellent activity than the related known compounds.

TABLE III

| Structure | Biological Activity in $LD_{50}$'s | | | | |
|---|---|---|---|---|---|
| | Aphid | Mite | Southern Armyworm | MBB | House-fly |
| Parent-I | i | i | i | i | i |
| Brown-I | i | i | i | i | i |
| Applicant-I | 40 | i | 7 | 9 | 35 |
| Parent-II | 25 | 350 | 500 | 10 | 110 |
| Brown-II | 70 | i | 62 | 11 | 150 |
| Applicant-II | 50 | 500 | 9 | 9 | 15 |

TABLE III-continued

| Structure | Biological Activity in LD$_{50}$'s | | | | |
|---|---|---|---|---|---|
| | Aphid | Mite | Southern Armyworm | MBB | House-fly |
| Parent-III | 20 | i | 150 | 8 | 250 |
| Brown-III | i | i | 80 | 6 | i |
| Applicant-III | 8 | 500 | 6 | 3 | 24 |
| Parent-VI | 160 | 280 | 30 | 6 | 25 |
| Applicant-VI | i | 6 | 29 | 22 | 2 |

It will be understood that the insect species and other pests employed in the above tests are merely representative of a wide variety of pests that can be controlled by use of the novel compounds of this invention.

The compounds contemplated in this invention may be applied as insecticides, miticides and namatocides according to methods known to those skilled in the art. Pesticidal compositions containing the compounds as the active toxidant will usually comprise a carrier and-/or diluent, either liquid or solid.

Suitable liquid diluents or carriers include water, petroleum distillates, or other liquid carriers with or without surface active agents. Liquid concentrates may be prepared by dissolving one of these compounds with a nonphytoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents, for example, the condensation products of alkylene oxides with phenol and organic acids, alkyl aryl sulfonates, complex ether alcohols, quaternary ammonium compounds, and the like may be employed for this purpose.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects, mites and nematodes upon plants or other material to which the pesticides are applied. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are compatible with other constituents of the spray schedule, and they may be used in the soil, upon the seeds, or the roots of plants without injuring either the seeds or roots of plants. Mixtures of the active compounds may be employed if desired as well as combinations of the active compounds of this invention with other biologically active compounds.

What is claimed is:

1. A compound of the formula:

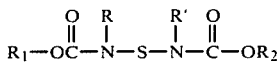

wherein: R and R' are individually alkyl radicals having from 1 to 4 carbon atoms;

$R_1$ is

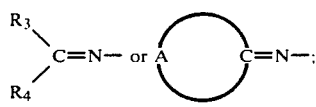

or $R_1$ is alkynyl when $R_2$ is other than alkenyl or alkynyl;

$R_2$ is other than $R_1$ and is alkenyl, alkynyl, phenyl, benzofuranyl, benzothienyl, naphthyl or tetrahydronaphthyl all of which may be either unsubstituted or substituted with one or more halogen, nitro, nitrile, alkyl, alkylthio, alkylthioalkyl, methylenedioxy, amino, alkylamino, dialkylamino, alkoxycarbonylamino, dialkylamino-alkylene-imino, alkylcarbonylamino, formylamino, dicyanoethylidene, alkoxy, alkynyloxy, phenoxy, phenyl, 2-dithianyl, 2-dithiolanyl, 2-dioxalanyl, 2-oxathianyl, 2-oxathiolanyl or 2-dioxanyl groups in any combination; or $R_2$ is:

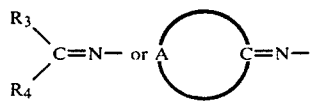

$R_3$ is hydrogen, alkyl, alkylthio or cyano;
$R_4$ is alkyl, alkylthio, alkylthioalkyl, alkoxy, aroyl, alkanoyl or alkoxycarbonyl, all of which may be unsubstituted or aliphatically substituted in any combination with one or more cyano, nitro, alkylthio, alkylsulfinyl, alkylsulfonyl, alkoxy, aminocarbonyl, alkylaminocarbonyl or dialkylaminocarbonyl groups or $R_4$ is phenyl, aminocarbonyl, alkylaminocarbonyl, dialkylaminocarbonyl or an $R_5CONH$- or $R_5CON(alkyl)$-group where $R_5$ is hydrogen, alkyl or alkoxy; and A is a divalent aliphatic chain, completing a five or six member ring, which includes one or two divalent oxygen, sulfur, sulfinyl or sulfonyl groups and which may also include one divalent amino alkylamino or carbonyl group; in any combination or A may also complete a six membered ring which includes three divalent sulfur, sulfinyl or sulfonyl groups in any combination; provided that the total number of aliphatic carbon atoms in $R_3$, $R_4$ and A, individually, may not exceed eight and provided that $R_2$ may not be 4-oximino-1,3-dithiolanyl.

2. A compound according to claim 1 wherein $R_1$ is:

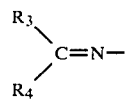

wherein $R_3$ is alkyl and $R_4$ is alkylthio or cyanoalkylthio.

3. A compound in accordance with claim 2 wherein $R_2$ is naphthyl.

4. A compound in accordance with claim 3 wherein $R_4$ is cyanoalkylthio.

5. A compound in accordance with claim 2 wherein $R_2$ is tetrahydronaphtyl.

6. A compound in accordance with claim 5 wherein $R_4$ is cyanoalkylthio.

7. A compound in accordance with claim 1 wherein $R_1$ is:

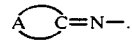

8. A compound in accordance with claim 7 wherein $R_2$ is naphthyl.

9. A compound in accordance with claim 7 wherein $R_2$ is tetrahydronaphthyl.

10. A compound according to claim 2 wherein $R_2$ is:

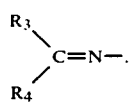

wherein $R_3$ is alkyl and $R_4$ is alkylthio.

11. N-[2-Methylthio-2-methylpropionaldehyde O-(N-methylcarbamoyl)oxime]N-[1-(N-methylcarbamoyloxy)-naphthalene]sulfide.

12. N-[1-Methylthioacetaldehyde O-(N-methylcarbamoyl)oxime]N-[1-naphthyl-(N-methylcarbamate]sulfide.

13. N-[1-Methylthioacetaldehyde O-(N-methylcarbamoyl oxime]N-[4-tert-butylphenyl-(N-methylcarbamoyloxy)]sulfide.

14. N-[1-Methylthioacetaldehyde O-(N-methylcarbamoyl)oxime]N-[3-isopropylphenyl-(N-methyl-carbamoyloxy)]sulfide.

15. N-[1-Methylthioacetaldehyde O-(N-methylcarbamoyl)oxime]N-[2-isopropoxyphenyl-(N-methylcarbamoyloxy)]sulfide.

16. N-[1-Methylthioacetaldehyde O-(N-methylcarbamoyl)oxime]N-[4-nonylphenyl-(N-methylcarbamoyloxy)]sulfide.

17. An insecticidal, miticidal or nematocidal composition which comprises an acceptable carrier and an insecticidally, miticidally or nematocidally effective amount of a compound of the formula:

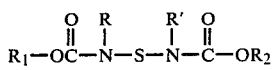

wherein: R and R' are individually alkyl radicals having from 1 to 4 carbon atoms;

R$_1$ is

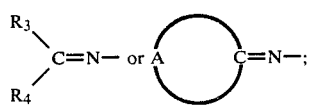

or

R$_1$ is alkynyl when R$_2$ is other than alkenyl or alkynyl;

R$_2$ is other than R$_1$ and is alkenyl, alkynyl, phenyl, benzofuranyl, benzothienyl, naphthyl or tetrahydronaphthyl all of which may be either unsubstituted or substituted with one or more halogen, nitro, nitrile, alkyl, alkylthio, alkylthioalkyl, methylenedioxy, amino, alkylamino, dialkylamino, alkoxycarbonylamino, dialkylamino-alkylene-imino, alkylcarbonylamino, formylamino, dicyanoethylidene, alkoxy, alkynyloxy, phenoxy, phenyl, 2-dithianyl, 2-dithiolanyl, 2-dioxalanyl, 2-oxathianyl, 2-oxathiolanyl or 2-dioxanyl groups in any combination; or R$_2$ is:

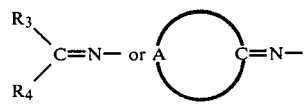

R$_3$ is hydrogen, alkyl, alkylthio or cyano;

R$_4$ is alkyl, alkylthio, alkylthioalkyl, alkoxy, aroyl, alkanoyl or alkoxycarbonyl, all of which may be unsubstituted or aliphatically substituted in any combination with one or more cyano, nitro, alkylthio, alkylsulfinyl, alkylsulfonyl, alkoxy, aminocarbonyl, alkylaminocarbonyl or dialkylaminocarbonyl groups or R$_4$ is phenyl, aminocarbonyl, alkylaminocarbonyl, dialkylaminocarbonyl or an R$_5$CONH- or R$_5$CON(alkyl)-group where R$_5$ is hydrogen, alkyl or alkoxy; and A is a divalent aliphatic chain, completing a five or six member ring, which includes one or two divalent oxygen, sulfur, sulfinyl or sulfonyl groups and which may also include one divalent amino alkylamino or carbonyl group; in any combination or A may also complete a six membered ring which includes three divalent sulfur, sulfinyl or sulfonyl groups in any combination; provided that the total number of aliphatic carbon atoms in R$_3$, R$_4$ and A, individually, may not exceed eight and provided that R$_2$ may not be 4-oximino-1,3-dithiolanyl.

18. A composition according to claim 17 wherein said compound is N-[2-Methylthio-2-methylpropionaldehyde O-(n-methylcarbamoyl)oxime]N-[1-(N-methylcarbamoyl)naphthalene]sulfide.

19. A composition according to claim 17 wherein said compound is N-[1-Methylthioacetaldehyde O-(N-methylcarbamoyl)oxime]N-[1-naphthyl-(N-methylcarbamate]sulfide.

20. A composition according to claim 17 wherein said compound is N-[1-Methylthioacetaldehyde O-(N-methylcarbamoyl)oxime]N-[4-tert-butylphenyl-(N-methylcarbamoyloxy)]sulfide.

21. A composition according to claim 17 wherein said compound is N-[1-Methylthioacetaldehyde O-(N-methylcarbamoyl)oxime]N-[3-isopropylphenyl-(N-methylcarbamoyloxy)]sulfide.

22. A composition according to claim 17 wherein said compound is N-[1-Methylthioacetaldehyde O-(N-methylcarbamoyl)oxime]N-[2-isopropoxyphenyl-(N-methylcarbamoyloxy)]sulfide.

23. A composition according to claim 17 wherein said compound is N-[1-Methylthioacetaldehyde O-(N-methylcarbamoyl)oxime]N-[4-nonylphenyl-(N-methylcarbamoyloxy)]sulfide.

24. A method of controlling insects, mites and nematodes which comprises subjecting them to an insecticidally, miticidally or nematocidally effective amount of a compound of the formula:

wherein: R and R' are individually alkyl radicals having from 1 to 4 carbon atoms;

R$_1$ is

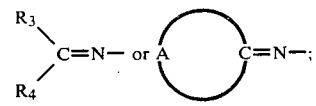

or

R$_1$ is alkynyl when R$_2$ is other than alkenyl or alkynyl;

R$_2$ is other than R$_1$ and is alkenyl, alkynyl, phenyl, benzofuranyl, benzothienyl, naphthyl or tetrahydronaphthyl all of which may be either unsubstituted or substituted with one or more halogen, nitro, nitrile, alkyl, alkylthio, alkylthioalkyl, methylenedioxy, amino, alkylamino, dialkylamino, alkoxycarbonylamino, dialkylamino-alkylene-imino, alkylcarbonylamino, formylamino, dicyanoethylidene, alkoxy, alkynyloxy, phenoxy, phenyl, 2-dithianyl, 2-dithiolanyl, 2-dioxalanyl, 2-oxathianyl, 2-oxathiolanyl or 2-dioxanyl groups in any combination; or R$_2$ is:

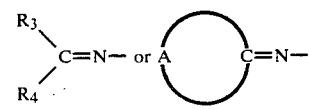

R$_3$ is hydrogen, alkyl, alkylthio or cyano;

R$_4$ is alkyl, alkylthio, alkylthioalkyl, alkoxy, aroyl, alkanoyl or alkoxycarbonyl, all of which may be unsubstituted or aliphatically substituted in any combination with one or more cyano, nitro, alkylthio, alkylsulfinyl, alkylsulfonyl, alkoxy, aminocarbonyl, alkylaminocarbonyl or dialkylaminocarbonyl groups or R$_4$ is phenyl, aminocarbonyl, alkylaminocarbonyl, dialkylaminocarbonyl or an R$_5$CONH- or R$_5$CON(alkyl)-group where R$_5$ is hydrogen, alkyl or alkoxy; and A is a divalent aliphatic chain, completing a five or six member ring, which includes one or two divalent oxygen, sulfur, sulfinyl or sulfonyl groups and which may also include one divalent amino alkylamino or carbonyl group; in any combination or A may also complete a six membered ring which includes three divalent sulfur, sulfinyl or sulfonyl groups in any combination; provided that the total number of aliphatic carbon atoms in R$_3$, R$_4$ and A, individually, may not exceed eight and provided that R$_2$ may not be 4-oximino-1,3-dithiolanyl.

25. A method according to claim 24 wherein said compound is N-[2-Methylthio-2-methylpropionaldehyde O-(N-methylcarbamoyl)oxime]N-[1-(N-methylcarbamoyloxy)-naphthalene]sulfide.

26. A method according to claim 24 wherein said compound is N-[1-Methylthioacetaldehyde O-(N-methylcarbamoyl)oxime]N-[1-naphthyl-(N-methylcarbamate]sulfide.

27. A method according to claim 24 wherein said compound is N-[1-Methylthioacetaldehyde O-(N-methylcarbamoyl)oxime]N-[4-tert-butylphenyl)-(N-methylcarbamoyloxy)sulfide.

28. A method according to claim 24 wherein said compound is N-[1-Methylthioacetaldehyde O-(N-methylcarbamoyl)oxime]N-[3-isopropylphenyl)-(N-methyl-carbamoyloxy)]sulfide.

29. A method according to claim 24 wherein said compound is N-[1-Methylthioacetaldehyde O-(N-methylcarbamoyl)oxime]N-[2-isopropoxyphenyl-(N-methylcarbamoyloxy)]sulfide.

30. A method according to claim 24 wherein said compound is N-[1-Methylthioacetaldehyde O-(N-methylcarbamoyl)oxime]N-[4-nonylphenyl-(N-methylcarbamoyloxy)]sulfide.

31. A compound of the formula:

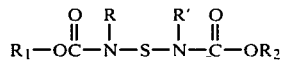

wherein: R and R' are individually alkyl radicals having from 1 to 4 carbon atoms;

R$_1$ is

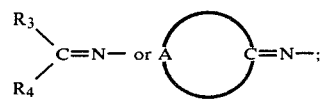

or

R$_1$ is alkynyl when R$_2$ is other than alkenyl or alkynyl;

R$_2$ is other than R$_1$ and is alkenyl, alkynyl, phenyl, benzofuranyl, benzothienyl, naphthyl or tetrahydronaphthyl all of which may be either unsubstituted or substituted with one or more halogen, nitro, nitrile, alkyl, alkylthio, alkylthioalkyl, methylenedioxy, amino, alkylamino, dialkylamino, alkoxycarbonylamino, dialkylamino-alkylene-imino, alkylcarbonylamino, formylamino, dicyanoethylidene, alkoxy, alkynyloxy, phenoxy, phenyl, 2-dithianyl, 2-dithiolanyl, 2-dioxalanyl, 2-oxathianyl, 2-oxathiolanyl or 2-dioxanyl groups in any combination; or R$_2$ is:

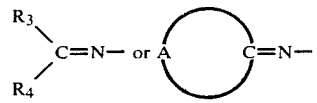

R$_3$ is hydrogen, alkyl, alkylthio or cyano;
R$_4$ is alkyl, alkylthio, alkylthioalkyl, alkoxy, aroyl, alkanoyl or alkoxycarbonyl, all of which may be unsubstituted or aliphatically substituted in any combination with one or more cyano, nitro, alkylthio, alkylsulfinyl, alkylsulfonyl, alkoxy, aminocarbonyl, alkylaminocarbonyl or dialkylaminocarbonyl groups or R$_4$ is phenyl, aminocarbonyl, alkylaminocarbonyl, dialkylaminocarbonyl or an R$_5$CONH- or R$_5$CON(alkyl)-group where R$_5$ is hydrogen, alkyl or alkoxy; and A is a divalent aliphatic chain, completing a five or six member ring, which includes one or two divalent oxygen, sulfur, sulfinyl or sulfonyl groups and which may also include one divalent amino alkylamino or carbonyl group; in any combination or A may also complete a six membered ring which includes three divalent sulfur, sulfinyl or sulfonyl groups in any combination; provided that the total number of aliphatic carbon atoms in R$_3$, R$_4$ and A, individually, may not exceed eight.

* * * * *